(12) United States Patent
Wollschläger

(10) Patent No.: US 6,695,818 B2
(45) Date of Patent: Feb. 24, 2004

(54) DEVICE FOR HANDLING A CATHETER

(76) Inventor: Helmut Wollschläger, Gabrielistrasse 9, Nürnberg (DE), D-90480

( * ) Notice: Subject to any disclaimer, the term of this patent is extended or adjusted under 35 U.S.C. 154(b) by 0 days.

(21) Appl. No.: 10/082,987

(22) Filed: Feb. 26, 2002

(65) Prior Publication Data

US 2002/0161355 A1 Oct. 31, 2002

Related U.S. Application Data

(63) Continuation of application No. PCT/DE00/02703, filed on Aug. 10, 2000.

(30) Foreign Application Priority Data

Aug. 27, 1999 (DE) .......................................... 199 40 785
Jun. 2, 2000 (DE) .......................................... 100 27 583

(51) Int. Cl.[7] .............................. A61M 5/32; F16K 7/04
(52) U.S. Cl. .......................................... 604/174; 251/7
(58) Field of Search ............................. 604/30, 33, 34, 604/174, 175, 177, 178, 243, 246, 249, 250, 256; 251/4, 7

(56) References Cited

U.S. PATENT DOCUMENTS

5,338,313 A  *  8/1994  Mollenauer et al. ........ 604/249
5,921,968 A  *  7/1999  Lampropoulos et al. .... 604/246
5,941,499 A  *  8/1999  Wollschlager ................. 251/4

* cited by examiner

*Primary Examiner*—Manuel Mendez
*Assistant Examiner*—Mark K. Han
(74) *Attorney, Agent, or Firm*—Harness, Dickey & Pierce, P.L.C.

(57) ABSTRACT

The invention relates to a device for handling a catheter. The inventive device is provided with a valve body (1). A lever arm (31) for actuating a pressure piston (9) and a flexible locking component (44) are mounted on said valve body. The lever arm (31) is interlocked with one of several detent noses (49) using the locking component. The lever arm (31) can thus be held in an interlocking position respectively. The locking component (44) is also provided with an actuating wing (50) which can be actuated with a little finger and is oriented in the direction of extension of the lever arm when the lever arm is in the interlocking position. Clamping forces which are exerted on a sealing plug (7) and serve for clamping the catheter can thus be variably adjusted with one hand by means of the pressure piston (9).

11 Claims, 2 Drawing Sheets funnel 12 passing into pressure piston recess 13

DEVICE FOR HANDLING A CATHETER

CROSS-REFERENCES TO RELATED APPLICATIONS

This application is a continuation of copending international patent application PCT/DE00/02703 filed on Aug. 10, 2000 and designating the U.S., which claims priority of German patent applications DE 199 40 785.1 filed on Aug. 27, 1999 and DE 100 27 583.4 filed on Jun. 2, 2000.

BACKGROUND OF THE INVENTION

The invention relates to a device for handling a catheter comprising a valve body on which a lever arm for actuating a pressure piston and a flexible locking component is mounted, wherein the lever arm can be held in an interlocking position by interlocking the lever arm with a detent nose using the locking component.

Such a device is known from DE 195 26 075 C1. In this device, a flexible locking component having a detent nose is integrally formed with a valve body for actuating a pressure piston by a lever arm, the pressure piston being inserted into said valve body. The locking component extends substantially perpendicular to the valve body. In the interlocking position, a clamping force is exerted on the catheter passing through the valve body and the pressure piston as to secure the catheter against an unintentional movement in an axial direction. However, it has turned out in practice that the device is usable only under certain restrictions, because on the one hand the unlocking of the lever arm is relatively complicated and on the other hand a higher flexibility in view of exerting a clamping force on the catheter would be advantageous.

Further devices are e.g. disclosed in U.S. Pat. No. 4,346,869, U.S. Pat. No. 5,338,313 and DE 33 24 699 C.

SUMMARY OF THE INVENTION

In view of the above, the object of the present invention is to provide a device of the aforementioned kind which allows to select different clamping forces being effective on the catheter wherein the forces to be exerted on the locking component are relatively low when operating with only one hand.

This object is solved by a device of the afore-mentioned kind, in which the locking component comprises a plurality of detent noses for interlocking the lever arm in a plurality of interlocking positions, and in which the locking component comprises an actuating wing, which is aligned in extension to the lever arm in the interlocking position of the lever arm.

Because the locking component comprises a plurality of detent noses and an actuating wing being aligned in extension to the lever arm, it is possible to unlock the lock and to bring the lever arm in a new position, for example in a new interlocking position by grasping the lever arm with two fingers of a hand, stretching out the little finger, putting the little finger on the actuating wing and exerting a relatively small pressure force on the actuating wing with a clamping force, which is exerted on the clamped catheter, being changed with respect to the initial interlocking position.

Advantageously, the locking component comprises at least two detent noses.

As to keep the lever arm's wear low, the lever arm is advantageously provided with a protruding snap-in pin.

For achieving a simple and safe interlock, it is advantageous that each detent nose is provided with a flank being aligned substantially parallel to the valve body and being located on the side facing the valve body, and with a tapered flank being located on the side opposite to the valve body.

In view of a design as anatomical as possible, it is intended to align the lever arm in its interlocking position parallel to a bend line of the lever arm.

As to achieve an operationally reliable handling, in one embodiment a slide blocking support is provided on the side of the actuating wing opposite to the valve body. Advantageously, the support is made of rubber, silicon or caoutchouc.

In a further embodiment, the side of the actuating wing opposite to the valve body is roughened, as to avoid a sliding-off of the little finger.

In order to keep the exerting pressure force as low as possible, the locking component is provided with at least one recess between the dent noses and the valve body for increasing the flexibility.

BRIEF DESCRIPTION OF THE DRAWINGS

Further embodiments and advantages of the present invention are subject of the following description of one embodiment with reference to the figures of the drawing. The drawings show.

DETAILED DESCRIPTION OF A PREFERRED EMBODIMENT

Figure 1:
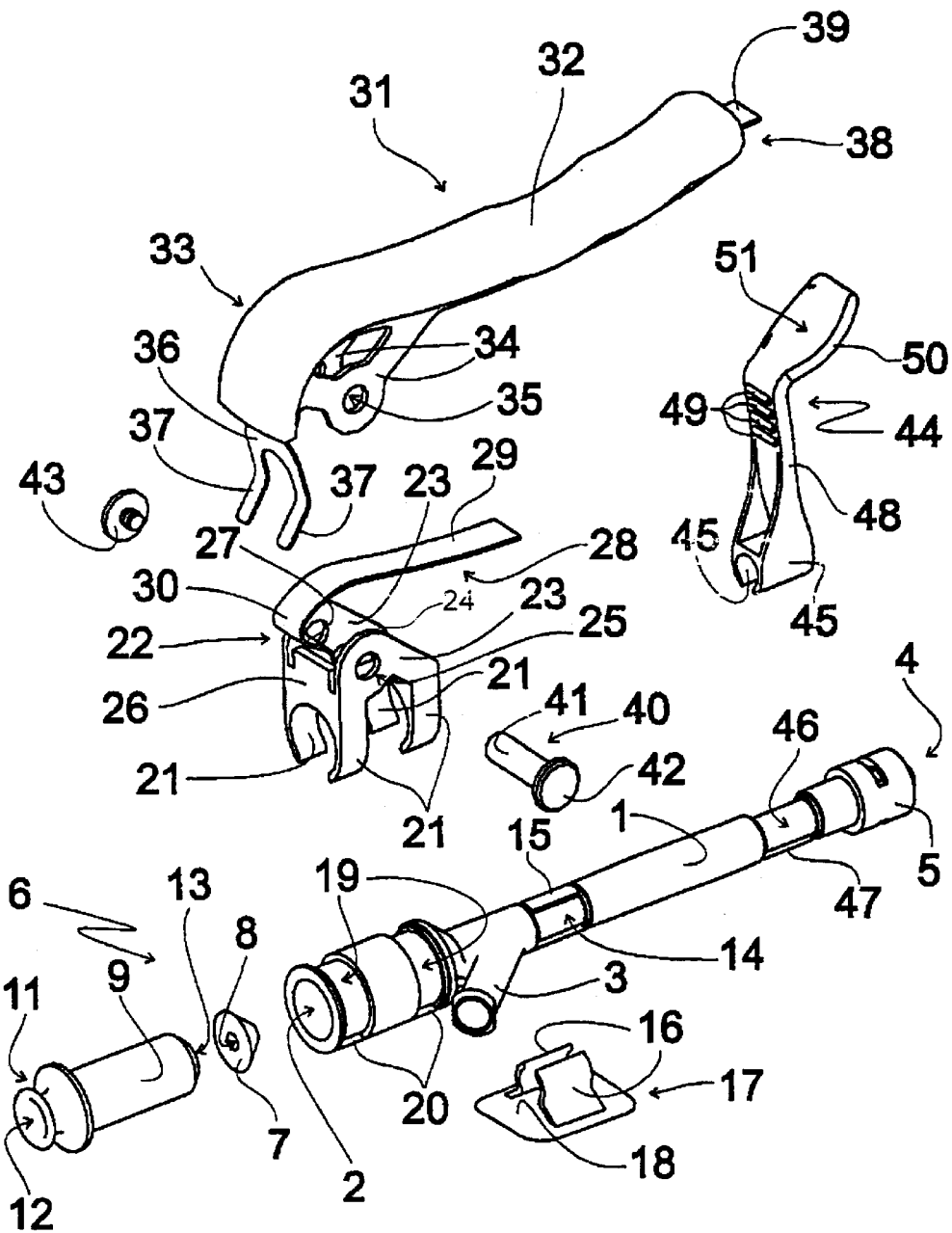
FIG. 1 a perspective exploded view of an embodiment of a device according to the present invention having a valve body detachably mounted on a lever arm as well as a detachably mounted locking component, and FIG. 2 a longitudinal section of the embodiment according to FIG. 1 with the lever arm being in an interlocking position.

FIG. 1 shows in a perspective exploded view an embodiment of a device according to the present invention. The device according to the present invention and FIG. 1 has an oblong valve body 1 which comprises an axial valve body passageway 2. Further, a side tube 3 is integrally mounted on the valve body 1 in an angular way.

When using the inventive device, a rotating sleeve 5 is provided at a connecting end 4 pointing away from a patient's body, which allows to seal the valve body in a known manner when a guiding catheter is inserted. At a sealing end 6 being opposed to the connecting end 4 and facing the patient's body when using the inventive device, a conically tapered sealing plug 7 made of a flexible material may be inserted into a conical receptacle of the valve body 1. The sealing plug 7 comprises a central plug passageway 8 for passing through a catheter.

Further, a pressure piston 9 may be inserted into the valve body passageway 2 at the sealing end 6, the pressure piston contacting the extensive flat side of the sealing plug 7 after being inserted. At the end opposite to the valve body 1, a ring collar 10 and a ring groove 11 are formed on the pressure piston 9, the ring collar having a cross section greater than that of the part being inserted into the valve body passageway 2. Finally, the pressure piston 9 comprises an inserting funnel 12 at the end adjacent to its ring collar 10, the inserting funnel 12 being tapered towards the valve body 1. The inserting funnel 12 passes into a pressure piston recess 13 formed in a longitudinal direction of the pressure piston 9 and having a substantially constant cross section.

In the valve body 1, a holding-up groove 14 is provided in a middle portion, which is formed as to extend in a radial and circumferential direction with the exception of a first stop bar 15. In the holding-up groove 14, spreadable holding-up cheeks 16 of a holding-up device 17 may be inserted. The holding-up device 17 comprises a flat supporting plate 18 which laterally protrudes the valve body 1 when the holding device 17 is put on the valve body 1. The holding device 17 is secured against an unintentional rotation by means of the stop bar 15.

In the area of the sealing end 6, two link bearing grooves 19 are formed and being spaced apart in axial direction of the valve body 1. The link bearing grooves 19 are substantially radially and circumferentially formed and extend up to second stop bars 20 radially opposing the first stop bar 15. Into the link bearing grooves 19, four spreadable link bearing cheeks 21 of a link bearing device 22 may be inserted. Each two opposed link bearing cheeks 21 pass over to side parts 23, which form a boundary of an inserting recess 24. The side parts 23 are each provided with an axis aperture 25, the aperture being aligned to each other.

On a front side 26 of the link bearing device 22 connecting the side parts 23, a fixing segment 27 of a curved leaf spring 28 is attached, the free end segment 29 of which being aligned such as to point away from the front side 26. Between the fixing segment 27 and the end segment 29, a spring segment 30 protruding the front side 26 is provided which substantially provides the spring effect of the leaf spring 28.

The device according to FIG. 1 further comprises a lever arm 31 which has an actuating segment 32 with a recessed grip and being designed along an anatomically curved line. At a link end 33 of the lever arm 31, lateral link bars 34 facing each other are provided. The link bars 34 have second axis apertures 35 facing each other and being aligned to each other. Finally, a spring fork 36 with two prongs 37 is attached at the link end 32, the prongs 37 are aligned substantially perpendicular with respect to the actuating segment 32. The spring fork 36 may be inserted into the ring groove 11 of the pressure piston 9.

A snap-in pin 39 is fixed to the actuating segment 32 at a snap-in end 38 opposed to the link end 32, the snap-in pin 39 protruding the actuating segment 32. In one embodiment, the snap-in pin is integrally formed with the lever arm 31. In another embodiment, the snap-in pin 39 is made of a wear-resistive rigid material, for example a metal, and is attached to the lever arm 31.

An inserting pin 40 is provided for attaching the link bearing device 22 to the lever arm 31. The inserting pin 40 may be inserted with its inserting pin segment 41 having a constant round cross section into the first axis aperture 25 of the link bearing device 22 and the second axis aperture 34 of the lever arm 31 which are aligned after inserting the link bars 34 into the inserting recess 24. The inserting pin 40 comprises at its one end a head 42 with an increased cross section compared to the inserting pin segment 41. The head 42 abuts one of the side parts 23 after inserting the inserting pin segment 41 and which prevents that the inserting pin 40 slides through. An inside thread is provided at the end of the inserting pin segment 41 opposite to the head 42, in which a lock nut 43 may be screwed in.

Finally, the inventive device according to FIG. 1 has a locking component 44 which may be inserted by means of locking component cheeks 45 into a radially and circumferentially extending locking component groove 46 formed in the valve body 1. The locking component groove 46 is bounded by a third stop bar 47 which is provided substantially in alignment with the second stop bars 22. The locking component 44 has a detent segment 48 in extension to the locking component cheeks 45. A plurality of detent noses 49 are formed on the detent segment 48. The detent segment 48 is flexible and advantageously provided with recesses not shown in FIG. 1 for increasing the flexibility. The detent segment 48 extends substantially perpendicular to the valve body 1 when the locking component 44 is put on the valve body 1. the detent segment 48 is followed by an actuating wing 50, which is formed highly angularly offset relative to the detent segment 48 and curved anatomically on the bend line of the lever arm 31. An actuating surface 51 of the actuating wing 50 which points away from the valve body 1 when the locking component 44 is put on the valve body 1, is preferably roughened or provided with a slide blocking support.

Figure 2:
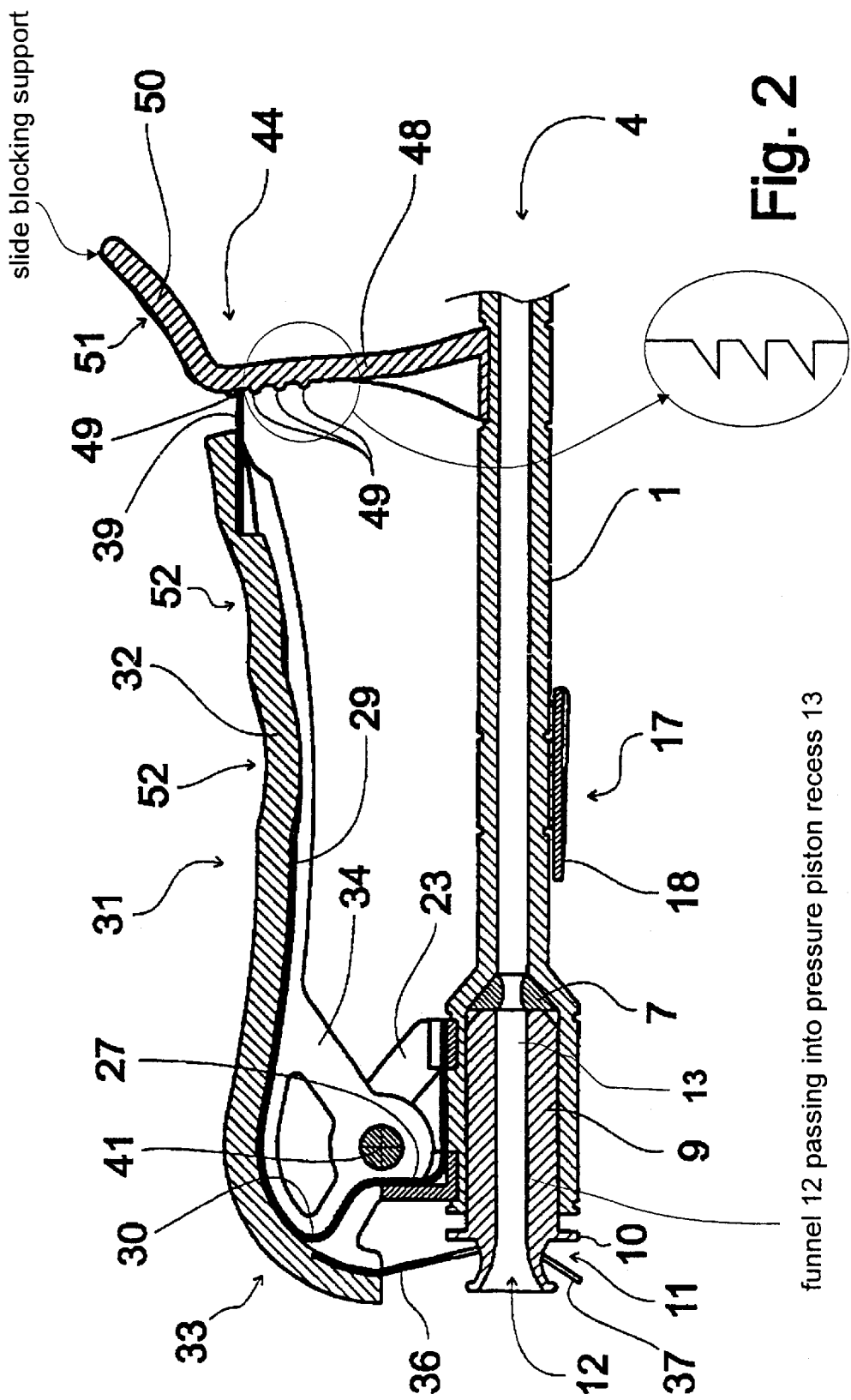

FIG. 2 shows a longitudinal section of the embodiment according to FIG. 1 with the lever arm 31 being in an interlocking position, in which the snap-in pin 39 of the lever arm 31 abuts against the detent nose 49 provided on the locking component 44. In this and any further interlocking position which may be achieved by abutting against the other detent noses 49, the spring fork 36 exerts a pressure on the pressure piston 9, the pressure being slightly lower compared with the unlocked position of the lever arm 31, so that the forces exerted on the sealing plug 7 and hence the clamping forces exerted on the catheter passing through the plug passageway 8 may be variably selected dependent on the interlocking position.

Moreover, the device according to the present invention may be handled with only one hand by putting the user's palm on the supporting plate 18 and by grasping the actuating segment 32 provided with recessed grips 52 of the lever arm 31 with the fingers. Thereby, the forefinger lies in the area of the link end 32 and the little finger in the area of the snap-in end 38. If a change of the position of the lever arm 31 is desired, the finger tip of the little finger is laid on the actuating surface 41 of the actuating wing 40 of the locking component 44 and exerts a pressure towards the valve body 1. As a result, the detent segment 48 may be bent with a relatively low compressive force and the respective detent nose 49 releases the snap-in pin 39. Now, the lever arm 31 may be brought in a new position, for example another interlocking position.

What is claimed is:

1. Device for handling a catheter, comprising a valve body to which a lever arm for actuating a pressure piston and a flexible locking component are attached, wherein by means of the locking component the lever arm may be held in an interlocking position by locking the lever arm with a detent nose, characterized in that the locking component comprises several detent noses for locking the lever arm in several interlocking positions and in that the locking component has an actuating wing, which is aligned in extension to the lever arm in the interlocking positions of the lever arm, further characterized in that the lever arm has a protruding snap-in pin.

2. Device according to claim 1, characterized in that the locking component comprises at least two detent noses.

3. Device according to claim 1, characterized in that each detent nose has a flank aligned substantially parallel to the valve body at the side facing the valve body, and a tapered flank at the side opposite to the valve body.

4. Device for handling a catheter, comprising a valve body to which a lever arm for actuating a pressure piston and a flexible locking component are attached, wherein by means of the locking component the lever arm may be held in an interlocking position by locking the lever arm with a detent nose, characterized in that the locking component comprises several detent noses for locking the lever arm in several interlocking positions and in that the locking component has an actuating wing, which is aligned in extension to the lever arm in the interlocking positions of the lever arm, further characterized in that the actuating wing in the interlocking positions is aligned parallel to the curved line of a lever arm.

5. Device for handling a catheter, comprising a valve body to which a lever arm for actuating a pressure piston and a flexible locking component are attached, wherein by means of the locking component the lever arm may be held in an interlocking position by locking the lever arm with a detent nose, characterized in that the locking component comprises several detent noses for locking the lever arm in several interlocking positions and in that the locking component has an actuating wing, which is aligned in extension to the lever arm in the interlocking positions of the lever arm, further characterized in that a slide blocking support is provided on the side of the actuating wing opposite to the valve body.

6. Device according to claim 5, characterized in that the support is made of rubber, silicon or caoutchouc.

7. Device according to claim 1, characterized in that the side of the actuating wing opposite to the valve body is roughened.

8. Device according to claim 1, characterized in that the locking component comprises at least one recess between the detent noses and the valve body for increasing its flexibility.

9. Device for handling a catheter, comprising a valve body to which a lever arm for actuating a pressure piston and a flexible locking component are attached, wherein by means of the locking component the lever arm may be held in an interlocking position by locking the lever arm with a detent nose, characterized in that said pressure piston comprises an inserting funnel, and further characterized in that the lever arm has a protruding snap-in pin.

10. Device according to claim 9, characterized in that said inserting funnel is tapered towards said valve body.

11. Device according to claim 10, characterized in that said inserting funnel passes into a pressure piston recess formed in a longitudinal direction of the pressure piston and having a substantially constant cross section.

* * * * *